(12) United States Patent
Balcke et al.

(10) Patent No.: US 9,259,378 B2
(45) Date of Patent: *Feb. 16, 2016

(54) EMULSIFIER-FREE, SKIN-CONDITIONING COSMETIC OR DERMATOLOGICAL PREPARATION

(71) Applicant: BEIERSDORF AG, Hamburg (DE)

(72) Inventors: Isabel Balcke, Hamburg (DE); Sabine Schulz, Hamburg (DE); Julia Eckert, Hamburg (DE); Guido Heinsohn, Glueckstadt (DE)

(73) Assignee: BEIERSDORF AG, Hamburg (DE)

( * ) Notice: Subject to any disclaimer, the term of this patent is extended or adjusted under 35 U.S.C. 154(b) by 29 days.

This patent is subject to a terminal disclaimer.

(21) Appl. No.: 13/948,873

(22) Filed: Jul. 23, 2013

(65) Prior Publication Data

US 2014/0308319 A1 Oct. 16, 2014

(30) Foreign Application Priority Data

Apr. 15, 2013 (DE) .......... 10 2013 206 718

(51) Int. Cl.
| | |
|---|---|
| A61K 8/04 | (2006.01) |
| A61K 8/31 | (2006.01) |
| A61K 8/34 | (2006.01) |
| A61Q 19/00 | (2006.01) |
| A61K 8/81 | (2006.01) |
| A61K 8/02 | (2006.01) |

(52) U.S. Cl.
CPC .......... *A61K 8/04* (2013.01); *A61K 8/0241* (2013.01); *A61K 8/31* (2013.01); *A61K 8/342* (2013.01); *A61K 8/8147* (2013.01); *A61K 8/8152* (2013.01); *A61Q 19/00* (2013.01); *A61Q 19/007* (2013.01); *A61K 2800/30* (2013.01); *A61K 2800/33* (2013.01); *A61K 2800/412* (2013.01); *A61K 2800/652* (2013.01)

(58) Field of Classification Search
None
See application file for complete search history.

(56) References Cited

U.S. PATENT DOCUMENTS

| | | | | |
|---|---|---|---|---|
| 3,146,170 | A | * | 8/1964 | Battista .......................... 424/59 |
| 4,992,476 | A | * | 2/1991 | Geria ...................... A61K 8/26 424/195.18 |
| 7,368,122 | B1 | * | 5/2008 | Dow et al. ..................... 424/407 |
| 2004/0228888 | A1 | * | 11/2004 | Kohlhase et al. ............. 424/401 |
| 2005/0112153 | A1 | * | 5/2005 | Wagoner ....................... 424/401 |
| 2005/0238605 | A1 | | 10/2005 | Kohlhase et al. |
| 2009/0281013 | A1 | | 11/2009 | Patel et al. |
| 2011/0071223 | A1 | | 3/2011 | Ishii et al. |
| 2013/0108572 | A1 | * | 5/2013 | Balcke .................. A61K 8/342 424/73 |

FOREIGN PATENT DOCUMENTS

| | | | |
|---|---|---|---|
| DE | 10246160 | A1 | 4/2004 |
| DE | 102004003435 | A1 | 8/2005 |
| DE | 102011013342 | A1 | 9/2011 |
| DE | 202012000164 | U1 | 1/2012 |
| DE | 202012000164 | * | 3/2012 |
| EP | 1090627 | A1 | 4/2001 |
| EP | 2174639 | A1 | 4/2010 |
| WO | 03075881 | A1 | 9/2003 |
| WO | 03094867 | A1 | 11/2003 |
| WO | 2013064391 | A2 | 5/2013 |

OTHER PUBLICATIONS

Cosing Cosmetics Directive, Paraffinum Liquidium, http://ec.europa.eu/consumers/cosmetics/cosing/index.cfm?fuseaction=search.details&id=35850, retrieved on line on Aug. 31, 2015.*

* cited by examiner

*Primary Examiner* — Jennifer A Berrios
(74) *Attorney, Agent, or Firm* — Abel Law Group, LLP

(57) ABSTRACT

Disclosed is an emulsifier-free, skin-conditioning, cosmetic or dermatological preparation. The preparation is obtainable by a process which involves, inter alia, the dispersion of one or more polyacrylic acid polymers in water and the mixing of the resultant dispersion with a molten lipid phase without complete homogenization of the phases.

19 Claims, 5 Drawing Sheets

EMULSIFIER-FREE, SKIN-CONDITIONING COSMETIC OR DERMATOLOGICAL PREPARATION

CROSS-REFERENCE TO RELATED APPLICATIONS

The present application claims priority under 35 U.S.C. §119 of German Patent Application No. 10 2013 206 718, filed Apr. 15, 2013, the entire disclosure of which is expressly incorporated by reference herein.

BACKGROUND OF THE INVENTION

1. Field of the Invention

The present invention relates to an emulsifier-free, skin-conditioning cosmetic or dermatological preparation and a method for its preparation. The preparation is obtainable by a specific method, which in turn brings about advantageous skin conditioning properties.

The preparation is suitable for application to wet skin without being completely rinsed off and therefore facilitates rubbing in cream while showering.

Rubbing in cream under wet conditions, skin care under the shower, is summarized as skin conditioning. This means, inter alia:
1. Use of a customary shower product for cleaning the skin, rinsing off
2. Application/spreading of the preparation according to the invention to wet skin
3. Showering off again with warm or cold water
4. Drying the skin.

2. Discussion of Background Information

Cosmetic or dermatological preparations can be divided on the basis of their application time and their intended use. Some products are washed off immediately after use ("rinse-off"), while others are intended to remain for longer on the skin and have an effect there ("leave-on").

Cosmetic preparations for caring for the skin are developed primarily for use on dry skin. These preparations are known as leave-on preparations, such as creams, lotions or body milk. They often are formulated as emulsions, in particular W/O, O/W, O/W/O or W/O/W emulsions.

Emulsions are generally understood as meaning heterogeneous systems which consist of two immiscible liquids or liquids that have only limited miscibility with one another, these usually being referred to as phases. In an emulsion, one of the two liquids (water or oil) is dispersed in the form of very fine droplets in the other liquid. The liquids (pure or as solutions) are present in an emulsion in a more or less fine distribution, which generally has only limited stability.

If the two liquids are water and oil, and oil droplets are present in fine distribution in water, the corresponding system is an oil-in-water emulsion (O/W emulsion, e.g. milk). The basic character, for example electrical conductivity, sensory properties, ability of the continuous phase to be colored, of an O/W emulsion is determined by the water phase. In the case of a water-in-oil emulsion (W/O emulsion, e.g. butter), the principle is reversed, the basic character here being determined by the oil.

Leave-on preparations are unsuitable for use on wet or moist skin. Due to the presence of emulsifiers therein, they can emulsify water and, due to the presence of lipids, sometimes leave behind an oily film.

By contrast, rinse-off preparations are designed for use under the shower or during bathing. By contrast, rinse-off preparations, however, involve to a lesser extent the care aspect as is obtained upon rubbing in cream.

It is desirable to provide a preparation which both takes into consideration the care aspect and can be applied as rinse-off, for example under the shower.

One property of cosmetic products that is very important to the consumer but can only be measured quantitatively with difficulty is their texture and sensory properties. The term "texture" is understood as meaning those properties of a cosmetic which are attributed to the constitution of the preparation, and can be perceived by sense of feel and touch and in some cases expressed in terms of mechanical or rheological flow properties. The texture can in particular be tested by means of sensorics. The texture of cosmetic products, which can optionally be influenced with the help of additives, and their effects which can be ascertained objectively are of virtually identical importance to the consumer.

The term "sensorics" refers to the scientific discipline which deals with the evaluation of cosmetic preparations on the basis of sensory impressions. The sensory assessment of a cosmetic is made on the basis of the visual, olfactory and haptic impressions.

visual impressions: all features that can be perceived by eye (color, shape, structure).

olfactory impressions: all odor impressions that can be perceived upon breathing in air through the nose, which can often be differentiated into initial scent (top note), main scent (medium note, body) and after-scent (base note). The volatile substances only released upon application also contribute to the olfactory impression.

haptic impressions: all sensations of the sense of touch which concern primarily constitution and consistency of the product.

The sensory analysis makes use of the possibility of ascertaining the overall sensory impression of a product integrally. Disadvantages of sensory analysis are the subjectivity of the impression, the ease with which the test subjects can be influenced and the considerable scattering of the results brought about as a consequence. These failings are nowadays countered by using groups of trained test subjects, mutual shielding of the testers, and statistical evaluation of the mostly extensive analytical data.

In view of the foregoing it would also be desirable to be able to provide preparations which, besides the criteria customary for cosmetics such as compatibility, storage stability and the like, also offer the consumer essential, hitherto unknown cosmetic, in particular sensory, benefits. In particular, the sought preparations should be suitable for use in the body care sector, i.e. for use on the entire body, and at the same time be sensorily attractive.

SUMMARY OF THE INVENTION

The present invention provides an aqueous skin-conditioning cosmetic or dermatological preparation which is suitable for application on wet or moist skin. The preparation is obtainable by a process which comprises
(a) dispersing one or more polyacrylic acid polymers in water to form a dispersion,
(b) melting one or more fatty alcohols and
    (b1) at least one (additional) wax and/or
    (b2) a mixture of liquid and solid hydrocarbons,
where at least the hydrocarbon mixture has a melting range of from 5° C. to 75° C., preferably of from 5° C. to 55° C. (according to DSC) to form a mixture,
(c) thoroughly mixing the dispersion and molten mixture obtained in (a) and (b) without achieving complete homogenization (i.e., discontinuing the mixing process before an essentially complete homogenization is achieved), and (d) optionally, adding one or more substances selected from neutralizing agents, skin moisturizers, preservatives, oils, thickeners and perfumes.

No emulsifiers are added to the preparation.

In one aspect, the preparation of the present invention may exhibit graininess. For example, at a layer thickness of 0.15 mm (+/−0.02 mm) the preparation may show an average of at least one crystallite having a particle size of from 5 to 500 μm per 4 mm$^2$ of area of layer of preparation.

In another aspect, the preparation may have a viscosity of at least 4,000 mPas, e.g., at least 6,000 mPas, at least 8,000 mPas, or at least 10,000 mPas.

In another aspect, the preparation may comprise components (b1) and (b2).

In yet another aspect of the preparation, at least two polyacrylic acid polymers, e.g., at least three polyacrylic acid polymers, may be dispersed in water and/or at least two fatty alcohols, e.g., at least three fatty alcohols may be melted.

In a still further aspect of the preparation of the present invention, the one or more polyacrylic acid polymers may comprise or may be selected from acrylates/C10-30 alkyl acrylate crosspolymers and carbomers and/or the preparation may comprise a total of from 0.05% to 2% by weight, e.g., a total of from 0.2% to 1% by weight or a total of from about 0.2 to about 0.5% by weight of the one or more polyacrylic acid polymers, based on the total weight of the preparation. For example, the preparation may comprise two different acrylates/C10-30 alkyl acrylate crosspolymers (having different properties) and one carbomer. The weight ratio of the two different acrylates/C10-30 alkyl acrylate crosspolymers may, for example, be from about 3:1 to about 1:3, e.g., from about 2:1 to about 1:2, or about 1:1. The weight ratio of the two different acrylates/C10-30 alkyl acrylate crosspolymers (together) to the carbomer may, for example be from about 20:1 to about 5:1, e.g., from about 12:1 to about 8:1, or about 10:1. For example, the preparation may comprise, based on the total weight of the preparation, from about 0.05% to about 0.2% by weight of an acrylates/C10-30 alkyl acrylate crosspolymer such as, e.g., Carbopol 3128), from about 0.05% to about 0.2% by weight of an acrylates/C10-30 alkyl acrylate crosspolymer such as, e.g., Pemulen TR-1, and from about 0.01% to 0.1% by weight of a carbomer (e.g., Carbopol 981).

In another aspect, the one or more polyacrylic acid polymers may comprise at least one polymer having emulsifying properties and/or at least one polymer which improves the sensory properties and/or increases the stability of the preparation, especially at elevated temperatures.

In another aspect of the preparation of the present invention, the one or more fatty alcohols may be C14-22 fatty alcohols or comprise at least one C14-22 fatty alcohol and/or the preparation may comprise a total of from 3% to 14% by weight, e.g., from about 4% to about 12% by weight, or a total of from 7% to 9% by weight of the one or more fatty alcohols, based on the total weight of the preparation. For example, the one or more fatty alcohols may comprise at least one $C_{14}$ fatty alcohol, at least one $C_{18}$ fatty alcohol and at least one $C_{16}/C_{18}$ fatty alcohol mixture and/or the one or more fatty alcohols may comprise at least two of myristyl alcohol, stearyl alcohol, and cetearyl alcohol. For example, in the weight ratio of the fatty alcohols C14, C18 and C16/18, a:b:c, a may range from about 0.5 to about 2, b may range from about 1 to about 3, and c may range from about 2 to about 6. For example, a may be 1, b may be about 2, and c may be about 5.

In another aspect, the preparation may comprise from about 0.5% to about 2% by weight (e.g., from about 1% to about 2% by weight) of $C_{14}$ fatty alcohols, from about 1% to about 4% by weight (e.g., from about 1.5% to about 3% by weight) of $C_{18}$ fatty alcohols and from about 2% to about 10% by weight (e.g., from about 4% to about 6% by weight) of $C_{16}/C_{18}$ fatty alcohol mixture, based on the total weight of the preparation.

In yet another aspect, the preparation of the present invention may comprise at least about 10% by weight, e.g., at least about 15% by weight and/or not more than about 30% by weight, e.g., not more than about 20% by weight of (b1) (e.g. microcrystalline wax), based on the total weight of the preparation.

In a still further aspect, the preparation of the present invention may comprise at least about 5% by weight, e.g., at least about 7% by weight and/or not more than about 12%, e.g. not more than 10% by weight of (b2), based on the total weight of the preparation. For example, the preparation may comprise weight ratio (b1):(b2) of from about 3:1 to about 1:1, e.g., about 2:1.

In another aspect, the preparation may comprise a total of component (b1) plus component (b2) of at least about 20% by weight, e.g., at least about 22% by weight, or at least 25% by weight and not more than about 45% by weight, e.g., not more than about 40% by weight, not more than about 35% by weight, or not more than about 30% by weight, based on the total weight of the preparation.

In another aspect, the preparation may be substantially free from surfactants.

In yet another aspect, the preparation of the present invention may comprise at least about 40%, e.g., at least about 45%, or at least about 50% by weight and/or not more than 70%, e.g., not more than about 65%, or not more than about 60% by weight of water, based on the total weight of the preparation.

In another aspect of the preparation of the present invention, the preparation may further comprise at least one moisturizer. For example, the at least one moisturizer may comprise glycerol and the preparation may comprise, for example, at least about 2% by weight, e.g., at least about 3% by weight, at least about 4% by weight, or at least about 5% by weight of glycerol, based on the total weight of the preparation.

The present invention also provides a process for preparing an emulsifier-free cosmetic or dermatological preparation, which process comprises (a) dispersing one or more polyacrylic acid polymers in water to form a dispersion, (b) melting one or more fatty alcohols and
  (b1) at least one (additional) wax and/or
  (b2) a mixture of liquid and solid hydrocarbons,
where at least the hydrocarbon mixture has a melting range of from 5° C. to 75° C. (according to DSC) to form a mixture, (c) thoroughly mixing the dispersion and molten mixture obtained in (a) and (b) without achieving complete homogenization, and (d) optionally, adding one or more substances selected from neutralizing agents, skin moisturizers, preservatives, oils, thickeners and perfumes.

The present invention further provides a method of conditioning skin, which method comprises applying to the skin the preparation of the present invention as set forth above (including the various aspects thereof).

In one aspect of the method, a skin care film may be formed on the skin after application of the preparation to the skin and subsequent rinsing with water, which film has a thickness of at least about 1 μm and/or comprises no skin-barrier-harming substances.

BRIEF DESCRIPTION OF THE DRAWINGS

In the accompanying drawings.

DETAILED DESCRIPTION OF THE PRESENT INVENTION

Figure 1:
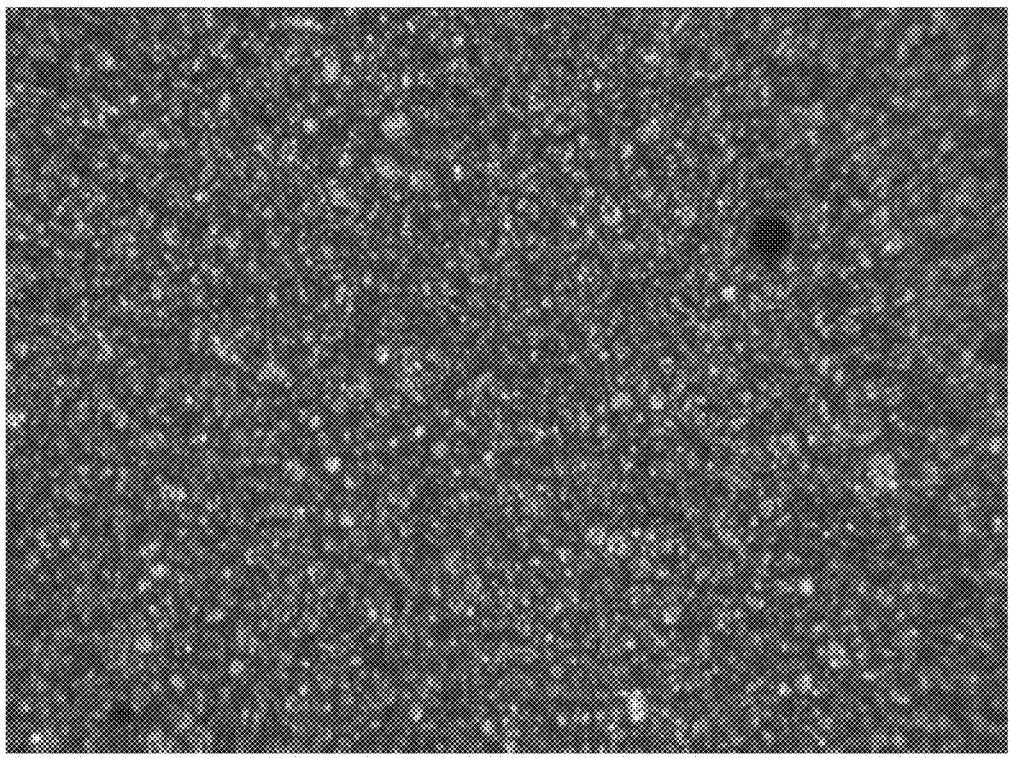
FIG. 1 shows a photograph of a layer of a preparation according to the present invention viewed under a transmitted-light microscope.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description in combination with the drawings making apparent to those skilled in the art how the several forms of the present invention may be embodied in practice.

In step (a) of the process for making the preparation of the present invention, dispersing of the one or more polymers in water will usually be accomplished by stirring (optionally with the additional application of heat) the one or more polymers into the water. However, other dispersion methods known to a person of skill in the art may be employed as well, such as, for example, use of a homogenizer or a high shear mixer, e.g., an Ultraturax (high input of energy). The term "dispersing" in the instant context also includes dissolving. In other words, at least at least a part of the one or more polyacrylic acids may be dissolved in water rather than merely be dispersed therein.

In this regard, it is to be appreciated that the preparations according to the present invention are obtainable in a different way than customary polyacrylic acid polymer-containing preparations. In particular, upon adding polyacrylic acid polymers to water a swelling is to be expected, meaning that higher energy is required in order to avoid ensuing clumping. For this reason, polyacrylic acid polymers are usually dispersed in oils. The known production practice therefore prescribes that the sometimes "dusty" polyacrylic acids should be predispersed in a lipid and only then be added to the water phase. In contrast thereto, according to the present invention the polyacrylic acid polymers are dispersed in water (without having been dispersed in a lipid beforehand). Surprisingly, this leads to the polyacrylic acid polymers being more "activated" as a result of this production mode than if they are wetted with lipid. This is evident inter alia from the fact that the preparation obtainable in this way forms for the first time a perceptible residue on the skin which can also be detected by the user.

When preparing the fatty phase in step (b), the one or more fatty alcohols are melted together with the one or more waxes (b1) and/or a mixture of liquid and solid hydrocarbons (b2). It is in accordance with the invention to mix in step (b) one or more fatty alcohols with one or more waxes, one or more fatty alcohols with a mixture of liquid and solid hydrocarbons, and one or more fatty alcohols with one or more waxes and a mixture of liquid and solid hydrocarbons.

The temperature employed in step (b) depends on the melting temperature of the individual constituents, and is preferably above 74° C.

Stirring is advantageously employed during the melting operation so that localized areas of overheating do not arise.

In step (c) the two phases obtained in step (a) and (b) are combined. It has surprisingly been found that if too much energy is introduced during step (c), i.e., if during the combining and mixing of the two phases a complete homogenization takes place, a satisfactory product cannot be obtained. In this case the resultant product is too smooth, too fine and too amorphous.

An incomplete homogenization of the phases obtained in steps (a) and (b) is essential to the present invention. "Incomplete homogenization" in the instant context means that optically anisotropic, i.e. crystalline areas, a so-called granular structure, can be observed under a polarizing microscope.

This granular structure, which differs from liquid crystalline structures, is described in more detail for example in the text book "Pharmazeutische Technologie [Pharmaceutical technology]"Kurt H. Bauer, Karl-Heinz Fromming, Claus Führer, Thieme Verlag, ISBN 3-13-692501-7, chapter 11, page 312 ff for hydrocarbon-containing preparations, vaselines. The entire disclosure of this document is incorporated by reference herein.

In a comparative experiment, customary polyacrylic acid polymer preparations, emulsion-based, were compared with preparations according to the invention (see Example below).

To prepare the sample, two microscope cover slips are placed on a microscope slide at a distance of about 1 cm. A small amount of the respective sample is placed between the cover slips and squeezed in order to obtain a layer thickness of the preparation of about 0.15 mm The sample is then viewed under a transmitted-light microscope equipped with two linear polarization filters (e.g. stereo microscope Motic DM-143 FBGG, with 4× zoom and 3 megapixel camera). Crossed linear polarization filters are used here in order to increase the optical contrast. A suitable magnification (20×) is selected and an image is taken with the digital camera.

FIGS. 1, 2, 3 and 6 show images obtained in this way.

Figure 2:
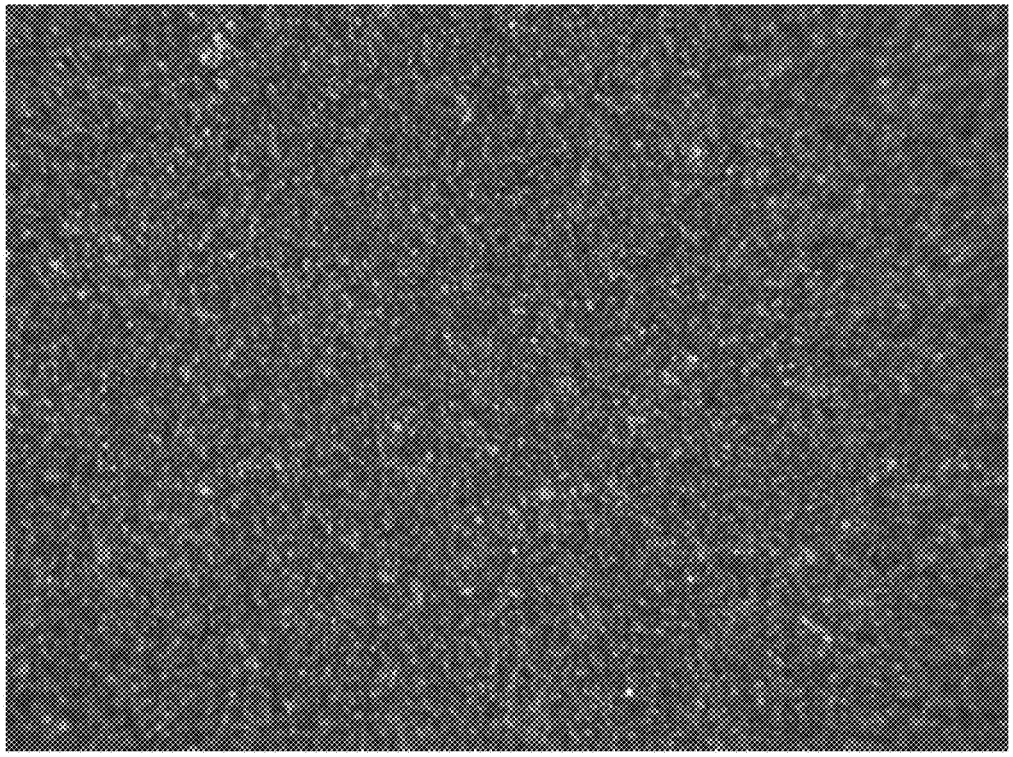
FIG. 2 shows a photograph of a layer of another preparation according to the present invention viewed under a transmitted-light microscope.
Figure 6:
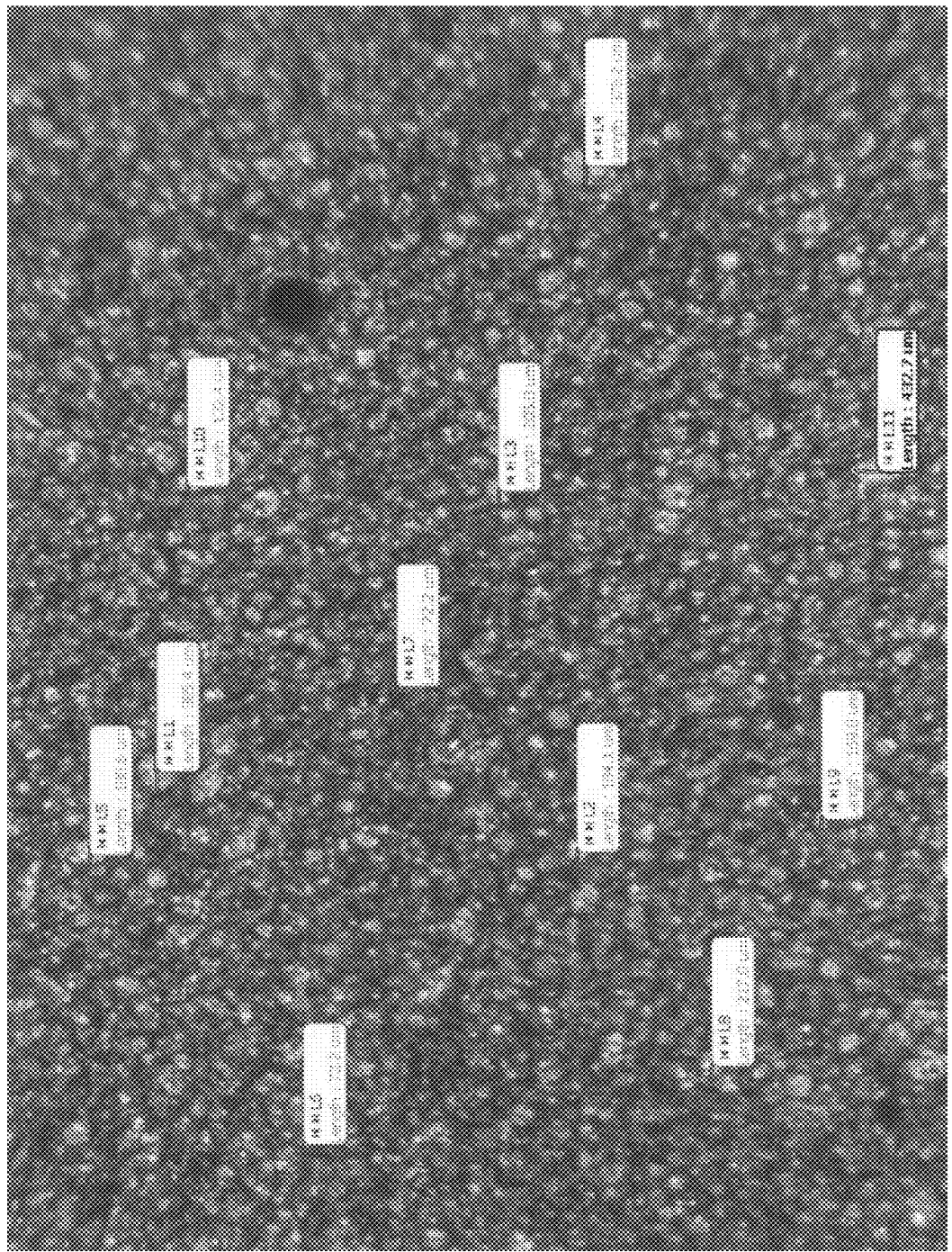
FIG. 6 shows a photograph of a layer of another preparation according to the present invention viewed under a transmitted-light microscope.

FIGS. 1, 2 and 6 show preparations according to the present invention with a recognizable granular structure, so-called crystallites. The preparations according to the invention have a so-called grainy performance, and are referred to as grainy.

Figure 3:
FIG. 3 shows a photograph of a preparation of the prior art viewed under a transmitted-light microscope.

In contrast to the preparations of the present invention the prior art preparations show a fine texture without recognizable granular structure or crystallites (FIG. 3).

According to the present invention a grainy texture preferably is characterized by the presence of at least one (e.g. at least 2, or at least 3) crystallites having a particle size in the range of from 5 to 500 µm per 4 $mm^2$ of the area of the preparation at a layer thickness of 0.15 mm (+/−0.02 mm)

This data is accessible and reworkable for example via the presented light microscopic investigations and shown by way of example in FIG. 6.

The particle size is a measure of the diameter of the particles. In other words, according to the invention, a completely homogeneous incorporation of the fatty phase into the aqueous phase is avoided so as not to obtain a smooth, fine product.

Only the so-called graininess constitutes the product performance of skin conditioning advantageous for the user. It was found that only this product property, which is brought about by the production process, leads to the preparations according to the invention. No smooth preparations are obtained by this process.

If a product is too smooth the product slides off from the skin too rapidly, a film cannot form and skin conditioning does not take place.

In this connection, smooth means inter alia that an excessively thin product with a viscosity of less than 4,000 mPas is obtained, which likewise does not bring about the desired product performance.

Preparations according to the invention therefore preferably exhibit a viscosity of at least 4,000 mPas (determined by using a Rheomat 123 from proRheo, spindle 1 at T=25° C.) and/or a granular structure which is characterized by the presence of on the average at least one crystallite having a particle size in the range of from 5 to 500 µm per 4 mm$^2$ area of the preparation at a layer thickness of 0.15 mm (+/−0.02 mm), determined by using a transmitted-light microscope equipped with two linear polarization filters and a 20-fold magnification.

The term "particle size" in the instant context is to be understood as follows. Particles are three-dimensional structures which may be solid and/or liquid and have a structure that can be distinguished from the surroundings.

The particles consist essentially of the fatty phase. These particles are distinguishable from the surroundings since they are stabilized by the gel network (surroundings). In this connection, a part of the fatty phase may also be present inside the gel network. What is decisive therefore is not a 100% separation between gel network (surroundings) and fatty phase, but the formation according to the invention of the granular structure with a particle density of on the average at least one crystallite with a particle size in the range of from 5 to 500 µm per 4 mm$^2$ area of the preparation.

Three parameters (length, width, height) are required in order to be able to give a complete description of particle sizes. In reality it is therefore difficult to describe a particle by stating a single number which corresponds to the particle size. In the majority of methods for determining size, it is therefore assumed that the material to be measured is spherical since a sphere is the only form which can be described using a single number (the diameter).

If the product comprises spherical particles, then the particle size is unambiguously defined by stating the sphere diameter, as according to the invention in the range of from 5 to 500 µm. However, the majority of the finely granular structures or crystallites does not consist of spheres, but of more or less irregularly shaped particles which may in an extreme case be needle-like, and in another case plate-like. The dispersity of the individual particles can be described here by the particle volume and additional parameters such as sphericity (sphere similarity). Instead of the single-parameter function for spheres, a multi-parameter dispersity function is obtained, the determination of which is associated with considerable measuring expenditure. Such expenditure is only justified if it serves to obtain essential information about product properties.

Consequently, it is normal in practice and also according to the invention to limit oneself to stating a single-parameter distribution function for the particle size, the diameter for an assumed spherical form of the particles.

The texture of the preparation according to the invention referred to as granular structure, particles, crystallites or graininess therefore essentially comprises fatty phase constituents which differ optically from the surroundings.

The care film which forms on the skin has been investigated in a further comparison, once after using a rinse-off product with integrated skin care aspects (Nivea cream soft shower gel) on its own (FIG. 4) and once after using the same product (Nivea cream soft shower gel) and subsequently using the preparation according to the invention (Example, FIG. 5). After both uses, the skin was rinsed with water.

The measurements carried out in relation to refatting of the skin were made by IR Imaging. The measurement technique is referred to as IR-ATR (InfraRed-Attenuated Total Reflectance).

It was found that only after using the preparation according to the invention does a care film that is detectable by means of the mentioned measurement technique remain on the skin. Detection takes place via the intensity of the hydrocarbon IR bands (CH-IR bands).

The care film that is obtainable by using the preparation according to the invention comprises a film which is formed on the skin and which comprises one or more lipids and/or skin moisturizers.

Figure 4:
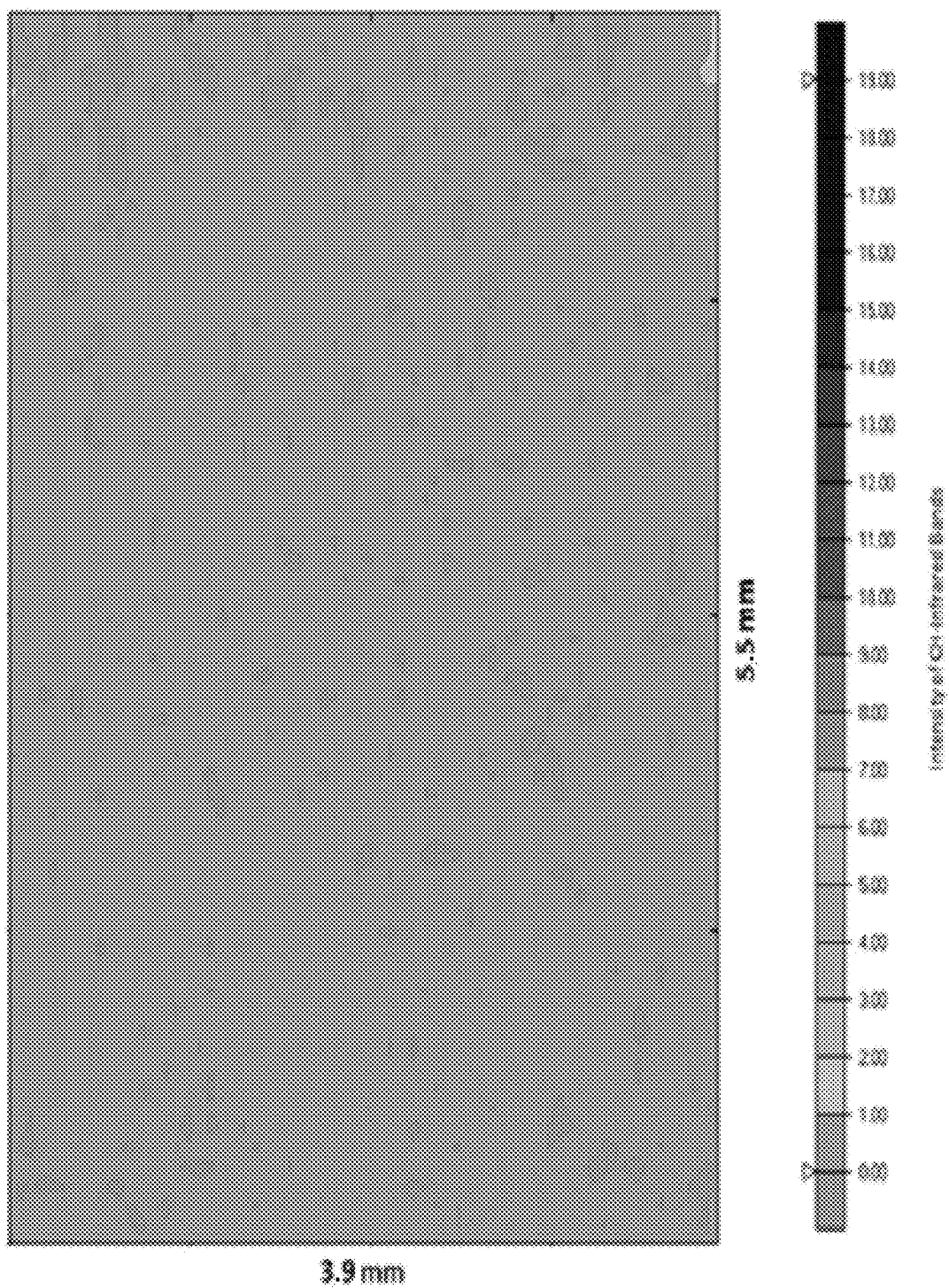
FIG. 4 is a representation of a layer of a preparation of the prior art based on data obtained by IR-ATR spectroscopy.
Figure 5:
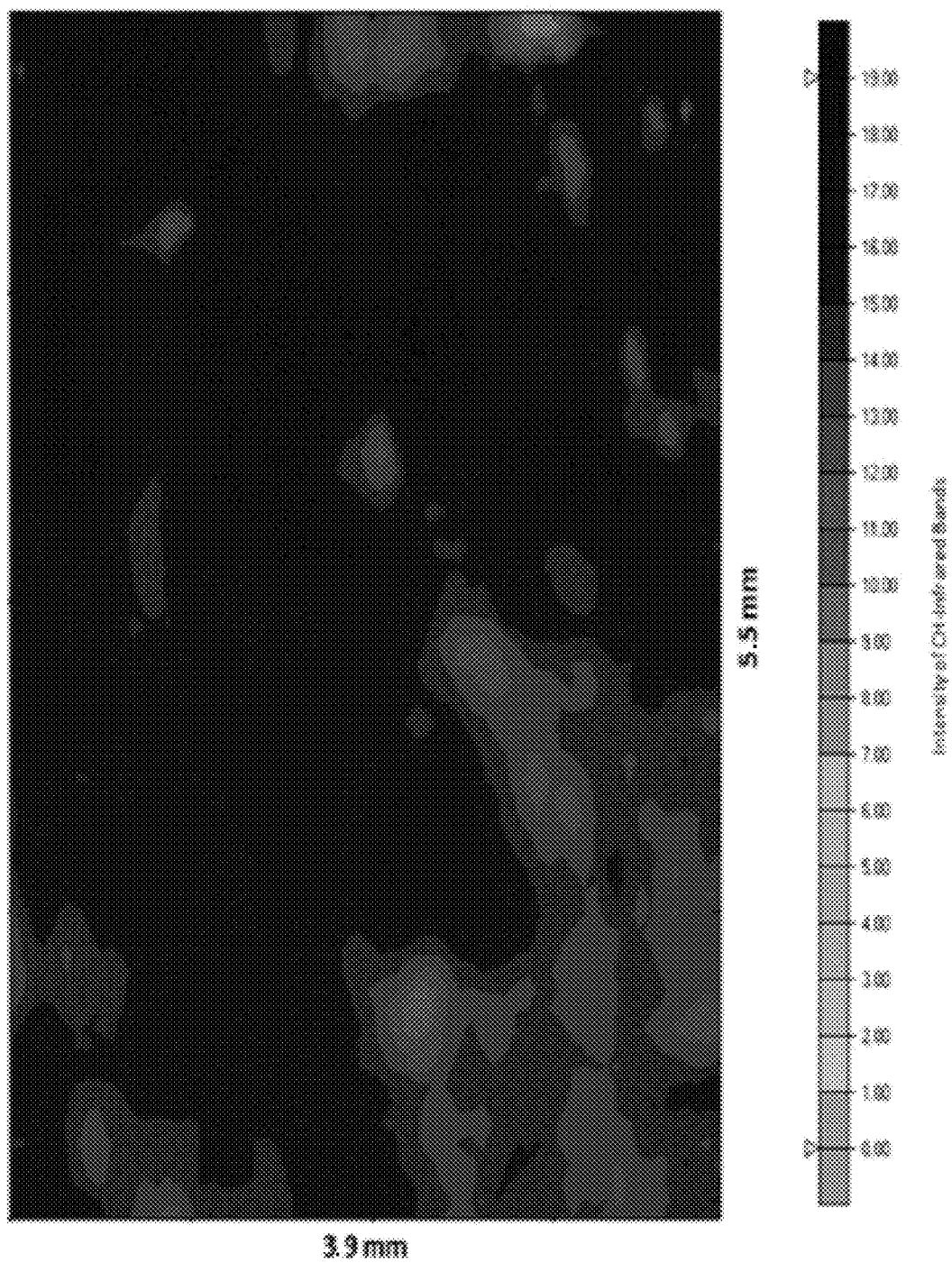
FIG. 5 is a representation of a layer of a preparation according to the present invention based on data obtained by IR-ATR spectroscopy.

FIGS. 4 and 5 show the comparison, the more gray the coloration, the more lipids there are on the skin. FIG. 5 shows a very significantly darker gray coloration than FIG. 4, which is proof of the presence of the care film that is obtained according to the present invention on the skin even after rinsing. The layer thickness of the film on the skin here is in the range of up to 10 µm, which can be derived from the infrared spectra and the measurement technology.

The skin conditioning according to the present invention comprises the rubbing in of cream under moist conditions, in particular skin care under the shower, where a care film remains on the skin even after rinsing. The care film can be detected by means of IR-ATR measurement technology and ideally has a thickness of at least about 1 µm and up to about 10 µm.

In particular, in the skin conditioning according to the present invention one or more lipids and/or skin moisturizers and substantially no skin-barrier-harming substances, in particular substantially no emulsifiers and/or surfactants, are present in the care film on the skin.

During the production of the preparation according to the invention one or more fatty alcohols and one or more waxes and/or a mixture of liquid and solid hydrocarbons, with a melting range from 5° C. to 75° C., preferably up to 55° C. (according to DSC), are melted.

Ideally, at least one fatty alcohol, at least one wax and a mixture of solid and liquid hydrocarbons are employed together.

Advantageous fatty alcohols include myristyl, cetearyl and/or stearyl alcohols, and advantageous waxes include microcrystalline wax (Cera Microcristallina). A preferred hydrocarbon mixture for use in the instant invention includes medical white oil, also called paraffinum liquidum. Medical white oils are substance mixtures which have a varying composition depending on origin. For example, products which have been obtained from geologically old Venezuelan petroleum are particularly rich in naphthenes (cycloalkanes). By contrast, the geologically young North Sea oil is low in naphthenes and comprises predominantly acyclic compounds. Preferably, naphthene-containing medical white oil is used in the preparation of the instant invention.

Advantageously, the fatty alcohol(s), wax(es) and hydrocarbon mixture all have a melting range of from 5° C. to 75° C., preferably up to 55° C. (according to DSC).

DSC (Differential Scanning calorimetry) is a thermal method for measuring the released/absorbed amount of heat of a sample during isothermal operation, heating or cooling (see DIN 53765, DIN 51007, ASTM E 474, ASTM D 3418). DSC is a comparative measurement method which permits the determination of amounts of heat of physical and chemical processes. If a material changes its physical state, such as e.g. melting or conversion of a crystal form to a different form or if it reacts chemically, heat is absorbed or released in the process. These amounts of heat can be measured quantitatively with the help of DSC. The method proceeds cyclically, meaning that after the first heating curve a defined cooling takes place and then the sample is heated once again in the stated temperature range. Two types of information are thus obtained: in the first heating curve, all thermal effects including past history are evident. In the second heating curve, the past history has been eliminated and the pure thermic behavior of the sample can be evaluated under defined cooling conditions. The melting range of the fatty alcohols, waxes and hydrocarbons between 4.5° C. and 75° C. according to DSC is the range ascertained in the first heating curve.

Waxes which can be used according to the invention also include fats and fat-like substances with wax-like consistency. These include inter alia fats (triglycerides), mono and diglycerides, natural and synthetic waxes, wax alcohols, esters of fatty alcohols and fatty acids, and also fatty acid amides or any desired mixtures of these substances.

The waxes are particularly preferably selected from the group of fats, in particular from the group of natural waxes such as, for example:

*Shorea stenoptera* seed butter, hydrogenated vegetable oil, hydrogenated coco-glycerides, *butyrospermum parkii* butter, *theobroma cacao* (cocoa) seed butter, mango butter, hydrogenated palm kernel glycerides, hydrogenated palm glycerides, sunflower seed wax, soybean glycerides, *butyrospermum parkii* unsaponifiables, wool wax, cera alba, beeswax, sugar cane wax, cera carnauba, candelilla wax, Japan wax, hydrogenated rapeseed oil, shellac wax, hydrogenated lecithin, hydrogenated soybean oil;

from the group of synthetic waxes, in particular from:
Cera Microcristallina, synthetic beeswax, synthetic wax, polyethylene, paraffin wax, ceresin, and ozokerite;
from the group of fatty acids, in particular from:
palmitic acid, stearic acid;
and from the group of fatty acid esters, in particular from:
cetearyl nonanoate, methyl palmitate, glyceryl tribehenate, glyceryl laurate, glyceryl stearate, cetyl palmitate; shea butter oleyl esters, and PEG-8 beeswax.

The one or more fatty alcohols used for making the preparation of the present invention are preferably selected from (e.g., essentially consist of) C14 to C22 fatty alcohols. Preferably, the fatty alcohols are selected from linear fatty alcohols, in particular myristyl alcohol ($C_{14}H_{30}O$), cetyl alcohol (or palmityl alcohol) ($C_{16}H_{34}O$), stearyl alcohol (or octadecyl alcohol) ($C_{18}H_{38}O$) and cetylstearyl alcohol (cetearyl alcohol), behenyl alcohol, lanolin alcohol, a mixture of cetyl alcohol (hexadecanol) and stearyl alcohol (octadecanol).

The total fraction of C14-22 fatty alcohols advantageously is from 3% to 14% by weight, in particular from 7% to 9% by weight, based on the total weight of the preparation.

The weight ratio of the fatty alcohols C14, C18 and C16/18 is preferably selected as a:b:c, with a=0.5 to 2:b=1 to 3:c=2 to 6, in particular as 1:2:5.

The weight fractions are therefore advantageously selected in the range 0.5-1.5% by weight C14 fatty alcohols (C14), 1.5-2.5% by weight C18 fatty alcohols (C18) and 4-6% by weight C16/C18 fatty alcohols (C16/18), based on the total weight of the preparation.

The hydrocarbon mixtures for use in the present invention preferably are hydrocarbon gels or mixtures of liquid and solid paraffin hydrocarbons. Preferably, the content of solid hydrocarbons in the hydrocarbon mixture is from 1% to 50%, particularly preferably from 10% and 30% by weight, based on the total weight of the hydrocarbon mixture. The use of hydrocarbon mixtures which form fringed micelles and/or paracrystalline structures is particularly advantageous.

The fraction of the hydrocarbon mixture in the preparation is advantageously from 1% to 50% by weight, in particular from 20% to 30% by weight, based on the total weight of the preparation.

On or more fatty alcohols, in particular two or three fatty alcohols, are necessarily present in the preparation according to the invention. In addition, one or more waxes are added to the preparation. Instead of or in addition to the one or more waxes, a mixture of hydrocarbons which are solid and liquid at room temperature can also be added.

Ideally, the preparation comprises all three constituents, one or more fatty alcohols, one or more waxes and a mixture of liquid and solid hydrocarbons.

Cosmetic or dermatological substances known to the person skilled in the art can be included in the preparation according to the invention. Of course, their addition must not adversely affect the skin-conditioning properties of the resulting preparation.

Thickeners, fillers and neutralizing agents may advantageously be added to the preparations of the present invention.

Thickeners are advantageously suitable for stabilizing the system and boost the skin-conditioning properties and the special skin feel of the preparations according to the invention.

An example of a preferred filler is aluminum starch octenylsuccinate, which likewise leads to an optimization of the skin feel by making the skin care film somewhat more velvety.

The neutralizing agent, if added, is advantageously sodium hydroxide solution so that the thickeners can form their gel network and a stable system is produced.

The preparation according to the invention is (substantially) emulsifier-free. In this regard it is to be appreciated that while the polyacrylic acid polymers for use in the preparation of the present invention may have an emulsifying effect they are not deemed to be emulsifiers. In other words, (substantially) no emulsifiers besides polyacrylic acid polymers are included in the preparation of the present invention.

The term "polyacrylic acid polymers" in the present context means polymers of acrylic acid and/or methacrylic acid and also acrylate crosspolymers known in cosmetics.

These polymers preferably are macromolecules with a high molecular weight ($>10^6$ g/mol), which comprise a backbone of polyacrylic acid and small amounts of polyalkenyl ether crosslinkages. They are also referred to as carbomers.

These water-soluble or dispersible polymers can bring about a significant increase in viscosity in the liquid in which they are dissolved or dispersed. This is due to the formation of carbomer microgels in the water.

Besides the carbomers, particularly preferred polyacrylic acid polymers for use in the preparations of the present invention are those acrylate crosspolymers which exert a polymeric emulsifier effect.

Polymeric emulsifiers are primarily polyacrylic acid polymers with a high molecular weight. These emulsifying polyacrylic acid polymers comprise a small lipophilic fraction in addition to the main hydrophilic fraction. Within the context of the present invention, very particular preference is given to acrylate crosspolymers with the INCI name "Acrylates/C10-30 Alkyl Acrylate Crosspolymer", available under the tradenames PemulenTR-1 and Pemulen TR-2 and also Carbopol 1342, Carbopol 1382 and Carbopol ETD 2020 from NOVEON.

The polyacrylic acid polymers for use in the preparations of the present invention are particularly preferably selected from acrylates/C10-30 alkyl acrylate crosspolymers and/or carbomers. Particular preference is given to acrylates/C10-30 alkyl acrylate crosspolymer Pemulen® TR-1, e.g. from Lubrizol and Carbopol® 3128 from Lubrizol.

In this connection, a specific combination of one or more polyacrylic acid polymers with an emulsifying effect, such as Pemulen TR-1 with one or more other polyacrylic acid polymers, such as Carbopol 3128, which improve the sensory properties and ensure the stability of the preparation, especially at elevated temperatures, and the connection with free water is preferred according to the invention.

Particular preference is given here to a combination of at least three polyacrylic acid polymers, where one polyacrylic acid polymer has an emulsifying effect, such as e.g. Pemulen TR-1 or Pemulen TR-2, another polyacrylic acid polymer improves the sensory properties and ensures the stability of the preparation, especially at elevated temperatures (e.g. Carbopol 3128), and a third polyacrylic acid polymer which improves the sensory properties upon absorbing free water (e.g. Carbopol 981).

Advantageously, therefore, preferably at least three polyacrylic acid polymers, in particular three polyacrylic acid polymers which differ in their properties, are employed in the method of making the preparation according to the present invention.

The fraction of polyacrylic acid polymers preferably is from about 0.05% to about 2% by weight, in particular from about 0.2% to about 1% by weight, based on the total weight of the preparation.

The preparation according to the invention is obtainable by the method set forth in the claims. In particular the combination of at least two polyacrylic acid polymers and at least two C14-22 fatty alcohols is advantageous in that it provides improved stabilization of the preparation. Further, the skin feel during application to moist/wet skin is not unpleasant, not waxy, harsh or squeaky.

According to the invention, in the case of two polyacrylic acid polymers or three polyacrylic acid polymers one polyacrylic acid polymer preferably differs from each of the others in at least one property. The substance group acrylates/C10-30 alkyl acrylate crosspolymers includes for example the commercial products Pemulen TR-1 and TR-2.

For example, there are Carbomers of grades A, B and C. These grades differ, for example in that they afford gels of different viscosities (United States Pharmacopeia, USP).

Moreover, according to the present invention a fraction of waxes or preferably a mixture of liquid and solid hydrocarbons with a melting range of from 4.5 to 75° C., in particular up to 55° C. according to DSC is employed.

Oils which can be added to the preparations according to the invention are advantageously nonpolar to medium-polarity lipids. Otherwise the stability is more difficult to establish due to the absence of emulsifier.

Within the context of the present disclosure, the expression "lipids" is used as a generic term for fats, oils, waxes and the like, as is entirely familiar to those skilled in the art. The terms "oil phase" and "lipid phase" are also used synonymously.

Oils and fats differ inter alia in their polarity. It is proposed to adopt the interfacial tension towards water as a measure of the polarity index of an oil or of an oil phase. Here, the greater the polarity of the oil phase, the lower the interfacial tension between this oil phase and water. According to the invention, the interfacial tension is considered to be one possible measure of the polarity of a given oil component.

The interfacial tension is the force which acts upon an imaginary line having a length of one meter that is located at the interface between two phases. The physical unit for this interfacial tension is classically calculated according to the force/length relationship and is usually expressed in mN/m (milliNewtons divided by meters). It has a positive sign if it strives to reduce the size of the interface. In the converse case, it has a negative sign.

Preferred lipids are moreover medicinal white oils and silicone oils, particularly preferably naphthene-containing medicinal white oils, and also mixing products thereof.

Preferred preparations according to the present invention include a preparation which comprises, based on the total weight of the preparation:

from about 10% to about 20% by weight of one or more waxes (e.g., microcrystalline wax);

from about 5% to about 10% by weight of a mixture of liquid and solid hydrocarbons (e.g., medical white oil);

from about 0.01% to about 0.1% by weight of (at least) one polyacrylic acid polymer A which improves the sensory properties upon absorbing free water (e.g. Carbopol® 981);

from about 0.05% to about 0.2% by weight of (at least) one polyacrylic acid polymer B having an emulsifying effect, (e.g. Pemulen® TR-1 and/or Pemulen® TR-2);

from about 0.05% to about 0.2% by weight of (at least) one polyacrylic acid polymer C which improves the sensory properties and ensures the stability of the preparation, especially at elevated temperatures (e.g. Carbopol® 3128);

from about 0.5% to about 2% by weight of myristyl alcohol;

from about 1% to about 4% by weight of stearyl alcohol; and from about 2% to about 10% by weight of cetearyl alcohol.

Polyacrylic acid polymer C and/or myristyl alcohol may optionally be absent from the above preparation.

The preparation according to the present invention may also comprise cosmetic auxiliaries and further active ingredients as are customarily used in cosmetic preparations such as, e.g., dyes and coloring pigments, moisturizing and/or humectant substances (such as, e.g., glycerol, urea, and certain amino acids), fillers (such as, e.g., aluminum starch octenylsuccinate), foam stabilizers, UV filter substances, electrolytes (e.g., sea salt), fragrance and organic solvents, provided they do not adversely affect the desired properties of the preparation.

The preparation of the present invention may moreover comprise one or more active ingredients which have a positive influence on skin. Active ingredients for use in the present invention preferably exhibit a skin moisturizing effect and/or strengthen the barrier function of skin and/or promote the restructuring of the connective tissue and/or support the function of dry skin and/or positively influence irritated skin (both sensitive skin in general and skin irritated by noxae such as UV light or chemicals) and/or reduce wrinkles and/or protect esthetically unattractive skin such as aged skin and/or improve the appearance of dry or rough skin and/or reduce hyperpigmentation, hypopigmentation, defective pigmentation and/or age spots and/or reduce itching and/or visible blood vessel dilation such as teleangiektasis or cuperosis.

Non-limiting specific examples of active ingredients which may be comprised in the preparation of the present invention include bioquinones such as, e.g., ubiquinone Q10, isoflavone and isoflavonoids as well as isoflavonoid containing plant extracts such as soy and clover extracts, flavonoids, genistein, arctiin, cardiolipin, anti-freezing proteins, hop extracts, hop-malt extracts, ascorbic acid and derivatives thereof, tocopherol and esters thereof, biotin, creatine, creatinine, propionic acid, green tea extracts and solutions, white tea extracts or solutions, sericosides, various extracts of licorice root, licochalcone A, silymarin, silyphos, dexpanthenol, ethanol, inhibitors of the prostaglandin metabolism and in particular, cyclooxygenase inhibitors, inhibitors of the leucotriene metabolism and in particular, 5-lipoxygenase inhibitors, inhibitors of the 5-lipoxygenase inhibitor protein, FLAP, folic acid, phytoene, flavone glycosides such as, e.g., α-glucosylrutin, carnitine, polydocanol, carotenoids, taurine, dihydroxyacetone, 8-hexadecene-1,16 dicarboxylic acid, retinol and esters thereof, vitamin E and derivatives thereof, long chain hyaluronic acids (e.g., those having an average molecular weight of from 1 to 3 million Dalton), and short chain hyaluronic acids (e.g., those having an average molecular weight of from 5,000 to 1 million Dalton).

The one or more active ingredients, if present, will usually be present in a total concentration of from about 0.1% to about 30% by weight, based on the total weight of the preparation.

The preparation according to the invention permits for the first time the application of skin care under the shower.

The preparation according to the invention is advantageously formulated only with preservatives having a solubility in water of more than 0.75% at 20° C. Due to the substantial absence of emulsifiers, the result may otherwise be destabilizations and crystallizing out. Preferably, the one or more preservatives include at least phenoxyethanol (solubility in water at 20° C. about 2.4% by weight); preferably, they will not include methylisothiazolinone and/or parabens such as methyl paraben. The absence of emulsifiers can otherwise lead to destabilizations and to crystallization.

The preparations according to the present invention are preferably also substantially free of surfactants. In other words, one or more surfactants are preferably present, if at all, in a concentration which does not noticeably reduce the surface tension. Usually, total concentrations of surfactants, if present at all, in the preparation of the present invention are not higher than about 0.02%, e.g., not higher than about 0.01%, or not higher than about 0.001% by weight, based on the total weight of the preparation. The same concentration ranges apply to emulsifiers, if present at all.

Surfactants are substances which reduce the surface tension of a liquid or the interfacial tension between two phases and facilitate or support the formation of dispersions. Surfactants have the effect that two liquids that are in fact not miscible with one another, such as for example oil and water, can be dispersed.

Furthermore, surfactants are described as amphiphilic substances which are able to dissolve organic nonpolar substances in water. As a consequence of their specific molecular structure with at least one hydrophilic molecular moiety and one hydrophobic molecular moiety, they provide for a reduction in the surface tension of water, wetting of the skin, ease of soil removal and dissolution, ease of rinsing off and—if desired—foam regulation.

The hydrophilic moieties of a surfactant molecule are mostly polar functional groups, for example $-COO^-$, $-OSO_3^{2-}$, $-SO_3^-$, whereas the hydrophobic moieties are generally nonpolar hydrocarbon radicals. Surfactants are generally classified according to type and charge of the hydrophilic molecular moiety. In this connection, it is possible to differentiate between four groups:
  anionic surfactants,
  cationic surfactants,
  amphoteric surfactants and
  nonionic surfactants.

Anionic surfactants generally have carboxylate, sulfate or sulfonate groups as functional groups. In an aqueous solution, they form negatively charged organic ions in an acidic or neutral medium. Cationic surfactants are characterized almost exclusively by the presence of a quaternary ammonium group. In aqueous solution, they form positively charged organic ions in an acidic or neutral medium. Amphoteric surfactants contain both anionic and cationic groups and accordingly behave in aqueous solution like anionic or cationic surfactants depending on the pH. In a strongly acidic medium, they have a positive charge and in an alkaline medium they have a negative charge.

Furthermore, detersive substances, such as, for example, cationic surfactants, in particular quaternary ammonium compounds, are known. A detersive substance is used in laundry detergents, dishwashing detergents, shampoos and shower gels and refers to the fraction of the formulation which influences the washing or cleaning performance. Detersive substances increase the "solubility" of grease and dirt particles in water which adhere to the laundry or to the body. They may be of natural or synthetic origin. They are differentiated into anionic, cationic, ampholytic or nonionic, depending on the nature of their charge.

Emulsifiers enable two immiscible liquids (for example oil in water) to be combined to give an emulsion. On account of the amphiphilic character, they penetrate into the oil with their fat-soluble moiety. As a result of the hydrophilic moiety, the oil droplet now formed by stirring can be "dispersed" in the aqueous environment. Emulsifiers primarily have no detersive, surface-active character.

Emulsifiers and surfactants can harm the barrier layer of the skin. It therefore is preferred to add neither emulsifiers nor surfactants to the preparations according to the present invention.

The preparations according to the invention may be used on wet skin and in particular also for shaving.

The preparation according to the invention can be used for conditioning the skin.

The preparation permits the generation of a skin care film after application of the preparation to the skin and subsequent rinsing with water.

The care film that is formed is ideally has a thickness of at least about 1 μm thick (measured according to IR-ATR measurement technology) and/or comprises no skin-barrier-harming substances, in particular no emulsifiers, surfactants, PEGs and/or organohalogen compounds.

The example below illustrates the method of making a preparation according to the present invention. The numeric values are weight percentages, based on the total weight of the preparation.

Example

|  | Preferred range | Example |
| --- | --- | --- |
| Water phase |  |  |
| Water | 50-60 | 53.8 |
| Acrylates/C10-30 Alkyl Acrylate Crosspolymer (Carbopol 3128) | 0.05-0.2 | 0.1 |
| Carbomer (Carbopol 981) | 0.01-0.1 | 0.02 |
| Acrylates/C10-30 Alkyl Acrylate Crosspolymer (Pemulen TR-1) | 0.05-0.2 | 0.1 |
| Fatty phase |  |  |
| Microcrystalline wax | 10-20 | 16.5 |
| Paraffinum Liquidum | 5-10 | 8.5 |
| Myristyl alcohol | 0.5-2 | 1.0 |
| Cetearyl alcohol | 2-10 | 5.0 |
| Stearyl alcohol | 1-4 | 2.0 |
| Hydrogenated cocoglycerides | 1-5 | 3.0 |
| Phenoxyethanol | 0.2-0.7 | 0.5 |
| Neutralizing phase |  |  |
| Sodium hydroxide solution 45% strength | 0.1-0.2 | 0.16 |
| Water | 1-3 | 2.0 |
| Perfume phase |  |  |
| Almond oil | 0.2-0.5 | 0.33 |
| Methylisothiazolinone | 0.05-0.1 | 0.09 |
| Perfume | 0.5-1 | 0.8 |
| Powder phase |  |  |
| Aluminum starch octenylsuccinate | 0.5-2 | 1.0 |
| Glycerol | 2-8 | 5.1 |

The constituents of the water phase are stirred at 25° C. for 4 min and then heated to 75° C. with stirring.

The constituents of the fatty phase are melted at 75° C. and stirred.

The water and fatty phases are combined with stirring at 75° C. while avoiding complete homogenization. This is achieved by establishing a grainy texture with an average of at least one crystallite having a particle size in the range of from 5 to 500 μm per 4 mm$^2$ area of the preparation in a layer thickness of 0.15 mm (+/−0.02 mm)

The neutralizing, perfume and powder phases are then added with cooling to about 30° C. and finally the mixture is stirred.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological preparation, wherein the preparation is free from emulsifiers, exhibits graininess and is obtainable by a process which comprises:
   (a) dispersing one or more polyacrylic acid polymers in water to form a dispersion,
   (b) melting one or more fatty alcohols and
      (b1) at least one wax and/or
      (b2) a mixture of liquid and solid hydrocarbons,
   where at least the hydrocarbon mixture has a melting range of from 5° C. to 75° C. according to DSC to form a mixture,
   (c) thoroughly mixing the dispersion and mixture obtained in (a) and (b) without effecting complete homogenization, incomplete homogenization causing the graininess of the preparation, and
   (d) optionally, adding one or more substances selected from neutralizing agents, skin moisturizers, preservatives, oils, thickeners and perfumes;
   and wherein the preparation comprises at least one crystallite which comprises at least the one or more fatty alcohols and the at least one wax (b1) and/or the mixture of liquid and solid hydrocarbons (b2).

2. The preparation of claim 1, wherein the preparation has a viscosity of at least 4,000 mPas.

3. The preparation of claim 1, wherein at least two polyacrylic acid polymers are dispersed in water and at least two fatty alcohols are melted.

4. The preparation of claim 3, wherein at least three polyacrylic acid polymers are dispersed in water.

5. The preparation of claim 4, wherein at least three fatty alcohols are melted.

6. The preparation of claim 1, wherein the one or more polyacrylic acid polymers are selected from acrylates/C10-30 alkyl acrylate crosspolymers and carbomers.

7. The preparation of claim 1, wherein the preparation comprises a total of from 0.05% to 2% by weight of the one or more polyacrylic acid polymers, based on a total weight of the preparation.

8. The preparation of claim 7, wherein the preparation comprises a total of from 0.2% to 1% by weight of the one or more polyacrylic acid polymers.

9. The preparation of claim 1, wherein the preparation comprises a total of from 3% to 14% by weight of the one or more fatty alcohols, based on a total weight of the preparation.

10. The preparation of claim 9, wherein the preparation comprises a total of from 7% to 9% by weight of the one or more fatty alcohols.

11. The preparation of claim 1, wherein the one or more fatty alcohols comprise at least one $C_{14}$ fatty alcohol, at least one $C_{18}$ fatty alcohol and at least one $C_{16}/C_{18}$ fatty alcohol mixture.

12. The preparation of claim 1, wherein the one or more fatty alcohols comprise at least two of myristyl alcohol, stearyl alcohol, and cetearyl alcohol.

13. The preparation of claim 1, wherein the preparation is free from surfactants.

14. The preparation of claim 1, wherein the preparation comprises at least 40% by weight of water, based on a total weight of the preparation.

15. The preparation of claim 1, wherein the preparation comprises not more than 70% by weight of water, based on a total weight of the preparation.

16. A process for preparing an emulsifier-free cosmetic or dermatological preparation, wherein the process comprises:
   (a) dispersing one or more polyacrylic acid polymers in water to form a dispersion,
   (b) melting one or more fatty alcohols and
      (b1) at least one wax and/or
      (b2) a mixture of liquid and solid hydrocarbons,
   where at least the hydrocarbon mixture has a melting range of from 5° C. to 75° C. (according to DSC) to form a mixture, (c) thoroughly mixing the dispersion and mixture obtained in (a) and (b) without effecting complete homogenization, incomplete homogenization causing the graininess of the preparation, and
(d) optionally, adding one or more substances selected from neutralizing agents, skin moisturizers, preservatives, oils, thickeners and perfumes;
and wherein the preparation comprises at least one crystallite which comprises at least the one or more fatty alcohols and the at least one wax (b1) and/or the mixture of liquid and solid hydrocarbons (b2).

17. The preparation of claim 1, wherein the one or more fatty alcohols, the at least one wax and the mixture of solid and liquid hydrocarbons are employed together.

18. The preparation of claim 1, wherein the at least one wax comprises microcrystalline wax.

19. The preparation of claim 18, wherein a weight ratio (b1):(b2) is from 3:1 to 1:1.

* * * * *